US010555790B2

(12) United States Patent
Paul et al.

(10) Patent No.: US 10,555,790 B2
(45) Date of Patent: Feb. 11, 2020

(54) FLEXIBLE SENSORS AND RELATED SYSTEMS FOR DETERMINING FORCES APPLIED TO AN OBJECT, SUCH AS A SURGICAL INSTRUMENT, AND METHODS FOR MANUFACTURING SAME

(71) Applicant: St. Jude Medical, Cardiology Division, Inc., St. Paul, MN (US)

(72) Inventors: Saurav Paul, Shoreview, MN (US); Troy T. Tegg, Elk River, MN (US); John P. Gerhart, Plymouth, MN (US); Tianhong Cui, St. Paul, MN (US); Miao Lu, Xiamen (CN)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 458 days.

(21) Appl. No.: 15/406,013

(22) Filed: Jan. 13, 2017

(65) Prior Publication Data

US 2017/0143441 A1 May 25, 2017

Related U.S. Application Data

(60) Division of application No. 14/948,816, filed on Nov. 23, 2015, now abandoned, which is a continuation of
(Continued)

(51) Int. Cl.
*A61B 90/00* (2016.01)
*G01L 5/16* (2006.01)
(Continued)

(52) U.S. Cl.
CPC ......... *A61B 90/06* (2016.02); *A61M 25/0067* (2013.01); *G01L 1/142* (2013.01);
(Continued)

(58) Field of Classification Search
CPC .......... A61B 18/1492; A61B 2090/065; A61B 2090/064; A61B 5/6885; A61B 90/06;
(Continued)

(56) References Cited

U.S. PATENT DOCUMENTS 3,999,284 A   12/1976 Bicher
RE30,183 E    1/1980 Popenoe
(Continued)

FOREIGN PATENT DOCUMENTS

EP   0 525 830 A1   3/1993
FR     2885410 A1   11/2006

*Primary Examiner* — Jonathan M Dunlap
(74) *Attorney, Agent, or Firm* — Dykema Gossett PLLC

(57) ABSTRACT

Methods of manufacturing a flexible force sensor include forming a first sensor part providing a plurality of spaced first electrode plates in an electrically non-conductive material. A second sensor part is also formed and includes a plurality of second electrode plates in an electrically non-conductive material. The second electrode plates are identical to the first electrode plates at least in terms of spacing. The first part is assembled to the second part such that each of the first electrode plates are aligned with and parallel to, yet spaced from, respective ones of the second electrode plates, establishing a plurality of capacitive sensing components. The first electrode plates are movable relative to the corresponding second electrode plates, establishing a variable gap therebetween. The sensor parts can be ring-shaped. The sensor parts can be formed via MEMS techniques, with the non-conductive material being a polymer.

20 Claims, 16 Drawing Sheets

Related U.S. Application Data application No. 13/391,514, filed as application No. PCT/US2010/046190 on Aug. 20, 2010, now Pat. No. 9,222,845.

(60) Provisional application No. 61/235,937, filed on Aug. 21, 2009.

(51) Int. Cl.
| | | |
|---|---|---|
| *G01L 1/14* | (2006.01) | |
| *A61M 25/00* | (2006.01) | |
| *A61B 18/14* | (2006.01) | |
| *A61B 5/00* | (2006.01) | |
| *G01L 5/165* | (2020.01) | |

(52) U.S. Cl.
CPC ............ *G01L 5/165* (2013.01); *A61B 5/6885* (2013.01); *A61B 18/1492* (2013.01); *A61B 2090/064* (2016.02); *A61B 2090/065* (2016.02); *A61M 2205/332* (2013.01); *G01L 1/14* (2013.01); *G01L 1/146* (2013.01); *Y10T 29/49117* (2015.01)

(58) Field of Classification Search
CPC .............. A61M 25/00; A61M 25/0067; A61M 2205/332; G01L 5/165; G01L 1/14; G01L 1/142; G01L 1/146
See application file for complete search history.

(56) References Cited

U.S. PATENT DOCUMENTS

| | | | |
|---|---|---|---|
| 4,719,538 A | 1/1988 | Cox | |
| 5,392,658 A | 2/1995 | Okada | |
| 5,437,196 A | 8/1995 | Okada | |
| 5,492,020 A | 2/1996 | Okada | |
| 5,661,235 A | 8/1997 | Bonin | |
| 6,159,761 A | 12/2000 | Okada | |
| 6,269,697 B1 | 8/2001 | Okada | |
| 6,865,943 B2 | 3/2005 | Okada | |
| 7,219,561 B2 | 5/2007 | Okada | |
| 7,415,896 B2 | 8/2008 | Khoury | |
| 7,533,582 B2 | 5/2009 | Okada | |
| 7,757,393 B2 | 7/2010 | Ayazi et al. | |
| 7,900,513 B2 | 3/2011 | Okada | |
| 8,048,063 B2* | 11/2011 | Aeby ............ | A61B 5/042 385/13 |
| 8,157,789 B2* | 4/2012 | Leo ............ | A61B 5/6885 600/182 |
| 8,435,232 B2* | 5/2013 | Aeby ............ | A61B 5/042 606/1 |
| 8,567,265 B2* | 10/2013 | Aeby ............ | A61B 5/0084 73/862.624 |
| 8,567,495 B2 | 10/2013 | Beck | |
| 8,596,111 B2* | 12/2013 | Dargahi ............ | G01N 3/40 73/774 |
| 8,864,757 B2* | 10/2014 | Klimovitch ............ | A61B 5/042 600/437 |
| 8,945,025 B2* | 2/2015 | Olson ............ | A61M 25/0041 600/585 |
| 9,078,563 B2* | 7/2015 | Cros ............ | A61B 5/0215 |
| 9,649,155 B2* | 5/2017 | Olson ............ | A61M 25/0041 |
| 9,949,793 B2* | 4/2018 | Olson ............ | A61M 25/0041 |
| 10,022,190 B2* | 7/2018 | Valsamis ............ | A61B 5/22 |
| 2003/0130615 A1 | 7/2003 | Tom | |
| 2006/0287700 A1* | 12/2006 | White ............ | A61B 5/0031 607/127 |
| 2007/0100332 A1 | 5/2007 | Paul et al. | |
| 2007/0123764 A1 | 5/2007 | Thao et al. | |
| 2007/0227257 A1 | 10/2007 | Harish et al. | |
| 2007/0261496 A1 | 11/2007 | Jonsson et al. | |
| 2008/0009750 A1* | 1/2008 | Aeby ............ | A61B 5/042 600/478 |
| 2008/0015568 A1 | 1/2008 | Paul et al. | |
| 2008/0117017 A1 | 5/2008 | Morimoto | |
| 2008/0275428 A1 | 11/2008 | Tegg et al. | |
| 2009/0160462 A1* | 6/2009 | Harish ............ | B60C 23/0408 324/686 |
| 2009/0177095 A1* | 7/2009 | Aeby ............ | A61B 5/0084 600/478 |
| 2010/0058583 A1* | 3/2010 | Cros ............ | A61B 5/0215 29/825 |
| 2010/0094163 A1* | 4/2010 | Deladi ............ | A61B 5/02154 600/561 |
| 2010/0168559 A1* | 7/2010 | Tegg ............ | A61M 25/0054 600/424 |
| 2010/0168620 A1* | 7/2010 | Klimovitch ............ | A61B 5/042 600/587 |
| 2012/0180575 A1 | 7/2012 | Sakano | |
| 2013/0172786 A1* | 7/2013 | Olson ............ | A61M 25/0041 600/587 |
| 2015/0073245 A1* | 3/2015 | Klimovitch ............ | A61B 5/042 600/373 |
| 2015/0112331 A1* | 4/2015 | Olson ............ | A61M 25/0041 606/41 |
| 2018/0280081 A1* | 10/2018 | Olson ............ | A61M 25/0041 |

\* cited by examiner

FLEXIBLE SENSORS AND RELATED SYSTEMS FOR DETERMINING FORCES APPLIED TO AN OBJECT, SUCH AS A SURGICAL INSTRUMENT, AND METHODS FOR MANUFACTURING SAME

CROSS-REFERENCE TO RELATED APPLICATIONS

This application is a divisional of U.S. application Ser. No. 14/948,816, filed Nov. 23, 2015 and entitled "Flexible Sensors and Related Systems for Determining Forces Applied to an Object, Such as a Surgical Instrument, and Methods for Manufacturing Same" which is a continuation of U.S. application Ser. No. 13/391,514, filed May 2, 2012 and entitled "Flexible Sensors and Related Systems for Determining Forces Applied to an Object, Such as a Surgical Instrument, and Methods for Manufacturing Same" which is a U.S. national stage application claiming priority under 35 U.S.C. § 371 to International Application Serial No. PCT/US2010/046190, filed Aug. 20, 2010, entitled "Flexible Sensors and Related Systems for Determining Forces Applied to an Object, Such as a Surgical Instrument", which claims priority to U.S. Provisional Patent Application Ser. No. 61/235,937, filed Aug. 21, 2009, entitled "Flexible Sensors and Related Systems for Determining Forces Applied to an Object, Such as a Surgical Instrument"; and the entire teachings of each of which are incorporated herein by reference.

BACKGROUND

The present disclosure relates to force sensors. More particularly, it relates to sensors and related systems for determining magnitude and direction of a force applied to an object, with particular usefulness with relatively small surface area objects such as various surgical instruments.

The need to detect or determine parameters associated with a force applied to an object arises in a plethora of situations. In this regard, force sensors (or load cells) are widely used to measure or monitor the forces of compression, tension, and shear. The two basic components of a force sensor are the sensing element(s) and circuit. The sensing element is oftentimes a strain gauge, which is comprised of a coil; the circuit is the connection of these gauges throughout the force sensor. While conventional force sensors are well-suited for many applications, the constraints associated with certain objects and/or end uses prevents their implementation.

For example, many surgical procedures entail introduction of a surgical instrument into the patient's anatomy. More generally, a distal end of the surgical instrument is inserted into and/or through various portions of the anatomy, and in some instances purposefully brought into contact with an anatomical target site. The caregiver may desire to know the forces being experienced by the distal end (e.g., as the distal end is inserted into the patient, various anatomical structures may be encountered; upon contact of the distal end with an anatomical structure and with further attempts to distally maneuver the surgical instrument, resistance of the anatomical structure to further movement of the distal end creates or applies a force onto the distal end). With the advent of minimally invasive and similar procedures in which only a small incision is made in the skin through which the surgical instrument is introduced, the surgeon cannot readily view a location of the distal end within the patient, let alone estimate forces at the distal end. Further, where the surgical instrument is elongated and/or formed of a relatively flexible or resilient material, forces at the distal end are not directly transferred to the proximal end otherwise being held by the surgeon; under these circumstances, the surgeon cannot rely upon a tactile "feel" at the proximal end to estimate force. Unfortunately, due to the relatively small size of many surgical instruments, conventional force sensors are simply not viable. Similar concerns arise with instruments or objects in many other technical fields.

In light of the above, a need exists for sensors and related systems capable of estimating or determining force experienced by an object to which the sensor is assembled, with particular application to small scale object or end uses.

SUMMARY

Some aspects in accordance with principles of the present disclosure relate to a method of manufacturing a flexible force sensor. The method includes forming a first sensor part including a plurality of first electrode plates in an electrically non-conductive material, with the first electrode plates being circumferentially spaced from one another. A second sensor part is also formed and includes a plurality of second electrode plates in an electrically non-conductive material. In this regard, the second electrode plates are identical to the first electrode plates at least in terms of circumferential spacing. Finally, the first sensor part is assembled to the second sensor part such that respective ones of the first electrode plates are aligned and parallel to, yet spaced from, respective ones of the second electrode plates to establish a plurality of capacitive sensing components. The first electrode plate of each of the sensing components is retained so as to be movable relative to the corresponding second electrode plate to establish a variable gap therebetween. In some embodiments, the sensor parts are ring-shaped, with the resultant sensor defining a central bore. In yet other embodiments, the sensor parts are formed via MEMS techniques, with the non-conductive material being a polymer (e.g., a photosensitive or thermoplastic polymer).

Other aspects in accordance with principles of the present disclosure relate to a system for estimating magnitude and direction of a force applied to an object. The system includes a sensor, an energy source, and a detector. The sensor includes a housing and at least three capacitive sensing components. The housing is adapted for assembly to the object, and the three capacitive sensing components are retained by the housing. In this regard, each of the sensing components includes first and second electrode plates arranged parallel to one another in a spaced-apart fashion to form a capacitor. The housing maintains the electrode plates such that the first electrode plate is movable or deflectable relative to the second electrode plate in response to a force placed upon the housing in establishing a variable gap therebetween. The energy source is electrically connected to the sensing components, as is the detector. With this construction, the energy source delivers energy to the sensing components, and the detector receives an output signal affected by the sensing components. The output signal varies as a function of a size of the gap associated with each of the sensing components and is indicative of a magnitude and direction of a force placed upon the housing. In some embodiments, the system further includes at least three inductors electrically connected to respective ones of the sensing components in establishing an LC circuit. An impedance detector is employed to monitor voltage versus frequency information in the output signal in response to a sweeping voltage applied to the sensing components, with spikes in the output signal varying as a function of changes in gaps of the capacitive sensing components. In related embodiments, a single wire is employed to deliver a single output signal from the commonly connected inductors; in other embodiments, a separate wire is provided for each capacitive sensing component/inductor.

Yet other aspects in accordance with principles of the present disclosure relate to methods of determining magnitude and direction of force applied to an object, such as a surgical instrument. Energy is applied to a sensor assembled to the object, with the sensor including a housing and at least three capacitive sensing components as described above. The object is subjected to a force of unknown magnitude and direction, with the force being transferred to the sensor housing via the object and sufficient to cause a change in a size of the gap associated with at least one of the sensing components. An output signal is received from the sensor, with this output signal being affected by the sensing components. Finally, the output signal is analyzed to determine a magnitude and direction of the force. In some embodiments, voltage versus frequency information is provided with the output signal and is indicative of a current across each of the sensing components. In this regard, analyzing the output signal includes designating a change in a frequency pitch of the voltage versus frequency information as being collectively indicative of magnitude and direction of the applied force, for example by comparing spikes in the voltage versus frequency curve with baseline values for each of the capacitive sensing components.

DETAILED DESCRIPTION

Figure 1:
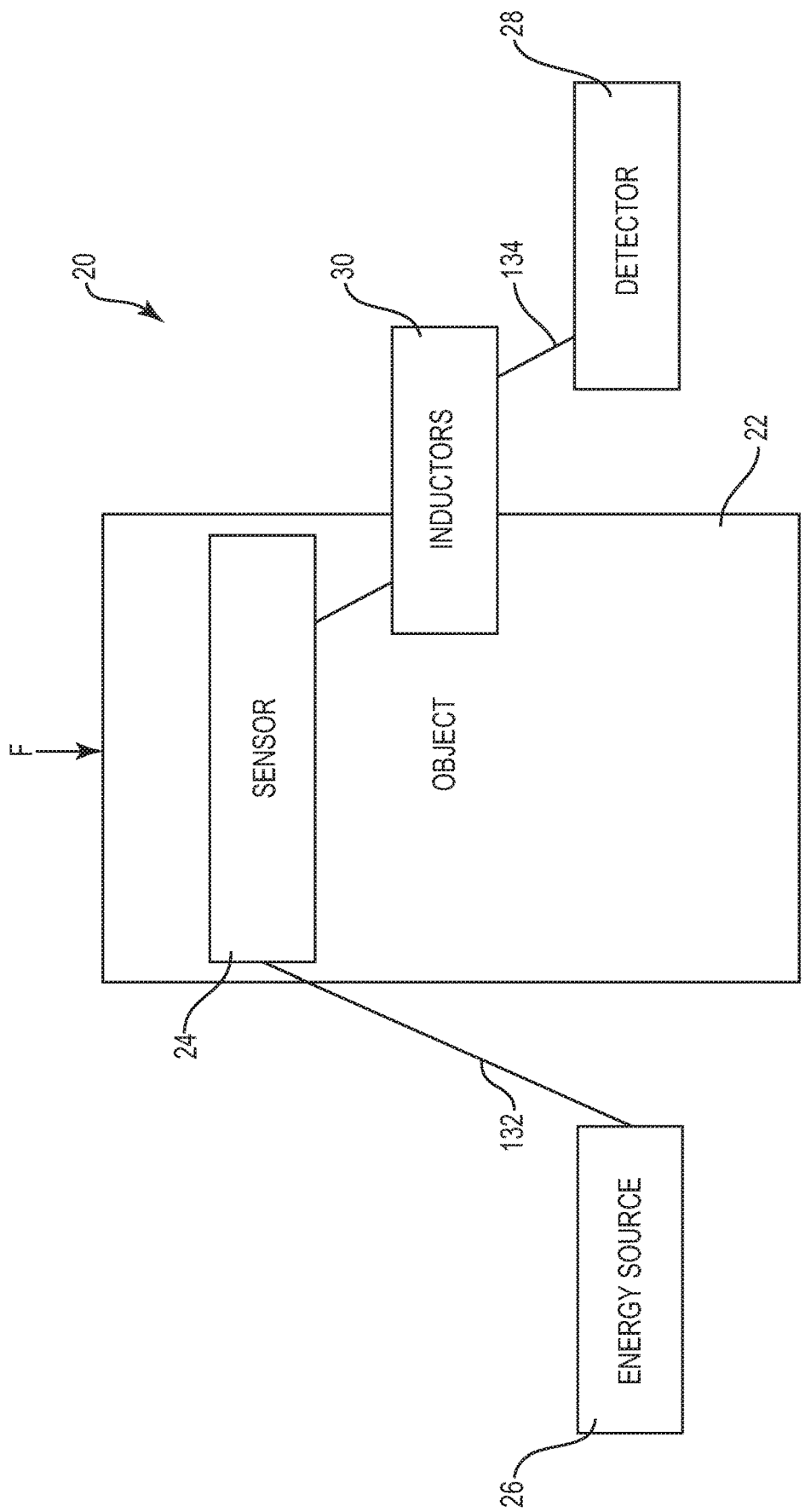
FIG. 1 is a block diagram of a force detection system in accordance with principles of the present disclosure.

One embodiment of a system 20 for determining magnitude and direction of a force F placed upon an object 22 is illustrated in block form in FIG. 1. The system 20 includes a sensor 24, an energy source 26, and a detector 28. Details on the various components are provided below. In general terms, however, the sensor 24 is assembled to the object 22, and includes three or more capacitive sensing elements. With this construction, inductors 30 can optionally be provided (assembled to, or separate from, the object 22) to establish an LC circuit. Regardless, the sensor 24 is located such that the force F, as applied to the object 22, is transferred onto the sensor 24. The energy source 26 applies energy to the sensor 24, and an output signal to the detector 28 is affected by the sensor 24. The effect of the sensor 24 upon the output signal varies as a function of the force F. As received at the detector 28, then, the output signal is indicative of the force F, and thus can be analyzed (e.g., via a computer (not shown) or other control electronics such as an ASIC state machine or a microprocessor) to determine the magnitude and direction of the force F.

As made clear below, the force detection system 20 can be employed with a plethora of differently sized and/or shaped objects. In some applications, however, the system 20, and in particular the sensor 24, is highly amenable for use with small scale objects 22 (or at small surface area regions of an object), and in particular with elongated, tubular objects.

Figure 2A:
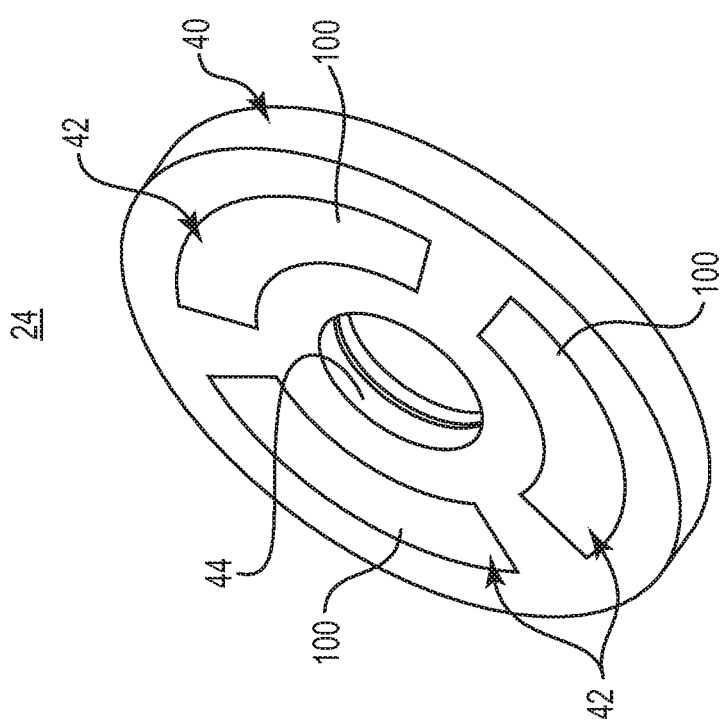
FIG. 2A is a perspective view of a sensor in accordance with principles of the present disclosure and useful with the system of FIG. 1.
Figure 2B:
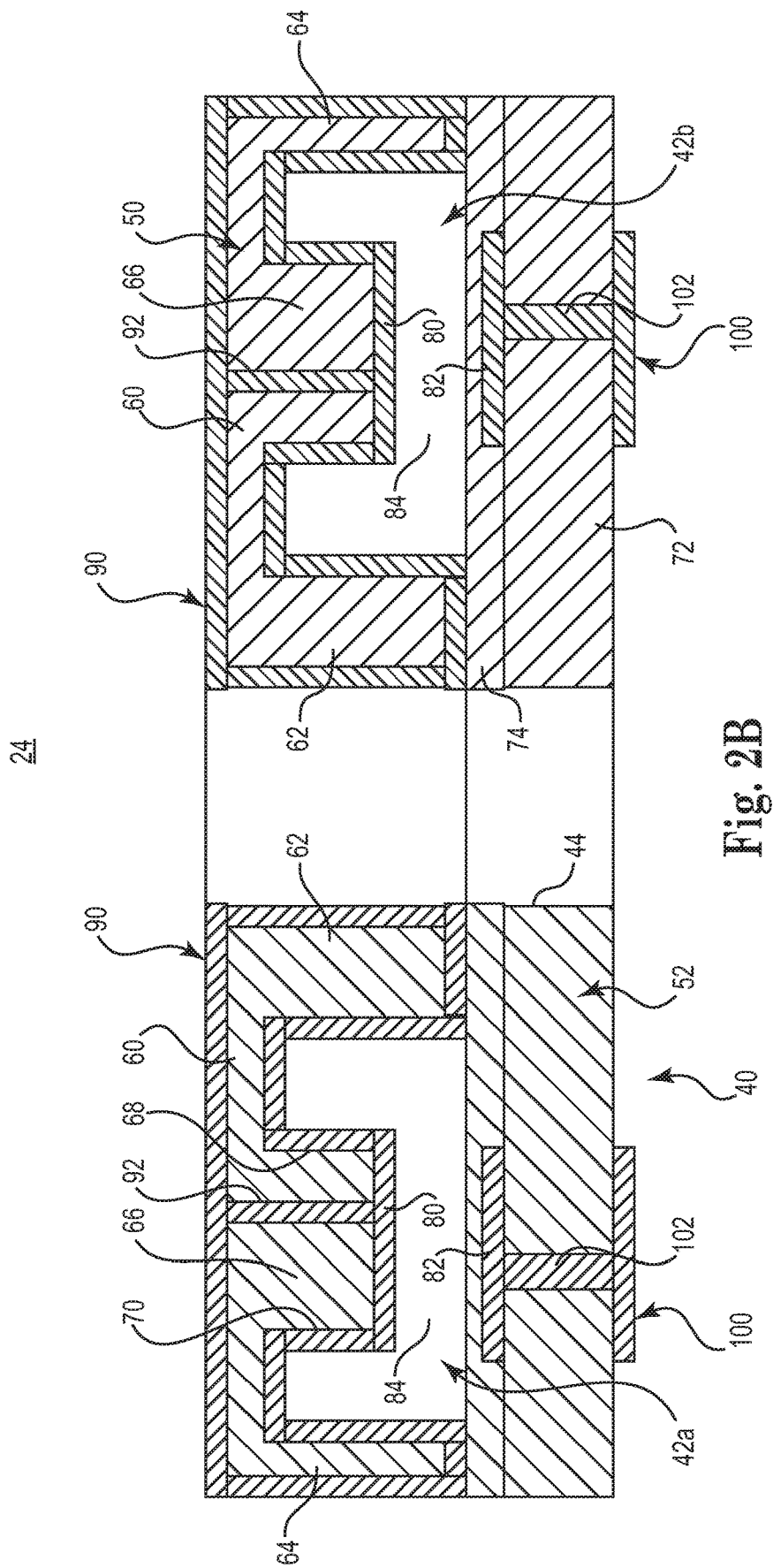
FIG. 2B is a simplified, cross-sectional view of the sensor of FIG. 2A.

With the above in mind, one embodiment of the sensor 24 is shown in FIGS. 2A and 2B, and includes a housing 40 and at least three capacitive sensing components 42. As a point of reference, the capacitive sensing components 42 are maintained within the housing 40, and thus are generally referenced in the view of FIG. 2A. The sensor 24 can assume a variety of shapes and/or sizes differing from those implicated by the illustrations of FIGS. 2A and 2B. Thus, while in some embodiments the sensor 24 is a cylindrical ring defining a central bore 44 as shown, other shapes that may or may not include the central bore 44 are also acceptable.

With specific reference to FIG. 2B, the housing 40 is generally comprised of a non-conductive material into which the capacitive sensing components 42, as well as other components as described below, are embedded or otherwise maintained. In this regard, the housing 40 exhibits at least a small degree of elastic or substantially elastic flexibility so as to permit alteration of an arrangement of each of the capacitive sensing components 42 in response to expected forces imparted upon the sensor 24 as described below.

In some embodiments, the housing 40 is formed or defined by first and second housing structures 50, 52. Relative to the orientation of FIG. 2B, the first housing structure 50 is an upper component, and formed from the non-conductive material to include or define a platform 60, inner and outer rims 62, 64, and a central region 66. The rims 62, 64 and the central region 66 project from the platform 60, with a thickness or height of the inner and outer rims 62, 64 being greater than that of the central region 66. With embodiments in which the sensor 24 forms or defines a cylindrical ring, the inner rim 62 is located at an inner diameter of the ring shape, whereas the outer rim 64 is located at an outer diameter. A first circumferential side 68 of the central region 66 faces, but is radially spaced from, the inner rim 62; similarly, an opposing, second circumferential side 70 of the central region 66 faces, but is radially spaced from, the outer rim 64. As described below, the elevated thickness inner and outer rims 62, 64 serve to offset the central region 66 from the second housing structure 52 upon final assembly. Finally, for reasons made clear below, the central region 66 can include circumferentially spaced sections that correspond with desired spacings of the various capacitive sensing components 42 (e.g., with embodiments having three of the capacitive sensing components 42, three circumferentially spaced central regions 66 are formed).

The second housing structure 52 is akin to the first housing structure 50, and includes a base 72 and an optional encapsulating layer 74. The second housing structure 52 is sized and shaped in accordance with the first housing structure 50 so that upon final assembly, the inner and outer rims 62, 64 interface with the second housing structure 52.

The housing structures 50, 52 can be formed from a variety of materials. In some embodiments in which the sensor 24 is intended for small scale applications (e.g., less than 5 mm in any dimension), the material(s) selected for the housing structures 50, 52 is conducive to MEMS construction (e.g., amenable to receiving sputter deposited metals). Thus, for example, the housing structures 50, 52 can be constructed of silicon. In yet other embodiments in which enhanced flexibility is desired and/or the sensor 24 is intended for use in surgical applications, the material of the housing structures 50, 52 can alternatively be a polymer or polymeric resin exhibiting biologically inert characteristics. For example, in some embodiments, the material of the housing structures 50, 52 can be a photosensitive or general thermoplastic resin, such as a negative, epoxy-type, near-UV photoresist material available under the trade designation SU-8 from Shell Chemical. Other materials are also acceptable. Finally, the housing structures 50, 52 should be elastically deformable (or substantially elastically deformable) in the presence of forces expected to be encountered during use. Thus, for example, the material selected for the first housing structure 50 in conjunction with the corresponding dimensions must permit inward deflection of the central region(s) 66 relative to the rims 62, 64 (e.g., bending along the platform 60) in response to an externally applied force, and return to the natural state of FIG. 2B upon removal of the force.

As indicated above, the sensor 24 includes at least three of the capacitive sensing components 42. The capacitive sensing components 42 are isolated from one another, with the cross-sectional view of FIG. 2B illustrating two of the sensing components 42a, 42b. While FIG. 2A has been described as generally reflecting provision of three of the capacitive sensing components 42, in other embodiments, four or more of the sensing components 42 are maintained by the housing 40.

Figure 3B:
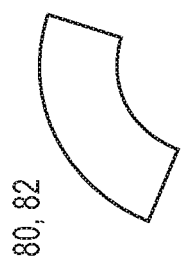
FIG. 3B is a top view of an electrode plate component of the sensor of FIG. 2A.
Figure 3A:
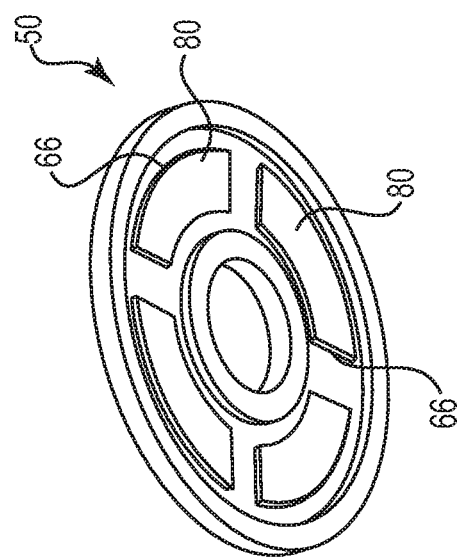
FIG. 3A is a interior, perspective view of a portion of the sensor of FIG. 2B.

Regardless of the number provided, the capacitive sensing components 42 are identical, and include a first electrode plate 80 and a second electrode plate 82. The first electrode plate 80 is mounted to the central region 66 of the first housing structure 50. FIG. 3A illustrates an interior of the first housing structure 50, with the first electrode plate 80 being formed on each of the circumferentially-spaced central regions 66 (it being understood that FIG. 3A reflects an alternative embodiment in which four of the central regions 66/first electrode plates 80, and thus capacitive sensing components 42 (FIG. 2B) are provided). Returning to FIG. 2B, the second electrode plate 82 is mounted to the base 72 of the second housing structure 52. Where provided, the optional encapsulating layer 74 covers or encapsulates the second electrode plate 82. The housing 40 retains the electrode plates 80, 82 in a substantially parallel alignment, with a gap 84 being established between the electrode plates 80, 82. With this arrangement, the spaced electrode plates 80, 82 define a parallel-plate capacitor. The sensing components 42 have, in some embodiments, an identical capacitance in the "normal" state of the housing 40 reflected in FIG. 2B (i.e., absence of external force-caused deflection of the first housing structure 50), dictated by a material, size and shape of the plates 80, 82, as well as a spacing of the gap 84. As a point of reference, for some small scale end uses (in which the sensor 24 has a maximum dimension of less than 5 mm), each of the capacitive sensing components 42 can have a capacitance on the order of 4 pF with the housing 40 in the "at rest" state.

The size and shape of the electrode plates 80, 82 can vary as a function of an overall size and shape of the sensor 24. With embodiments in which the sensor 24 is ring-shaped, the electrode plates 80, 82 can have an arcuate shape as shown, for example, in FIG. 3B. Alternatively, other shapes are acceptable. Regardless, the resultant capacitive sensing components 42 are arranged in a circular pattern.

Returning to FIG. 2B, the electrode plates 80, 82 are formed of a conductive material appropriate for capacitive interaction, such as metal. In some embodiments, the electrode plates 80, 82, as well as other conductive components associated with the sensor 24, are chromium/gold, although other materials are also acceptable.

Energy can be applied or delivered to the capacitive sensing components 42 in a variety of fashions. In some embodiments, the sensor 24 is constructed to include a common electrode 90 at an exterior of the first housing structure 50. A first conductor 92 is provide for each of the capacitive sensing components 42, electrically connecting the corresponding first electrode plate 80 with the common electrode 90 (e.g., the conductor 92 associated with the first capacitive sensor component 42a is separate from the conductor 92 provided for the second capacitive sensing component 42b). As shown, the conductor 92 is formed through a thickness of the first housing structure 50, extending through the central region 66 and the platform 60. Optionally, conductive material can be applied to other surfaces of the first housing structure 50 as shown in FIG. 2B for reinforcement.

The second electrode plate 82 is mounted on the platform 76 as shown. In some embodiments, the sensor 24 optionally further includes a conductive pad 100 for each of the capacitive sensing components 42. As a point of reference, FIG. 2A illustrates three of the conductive pads 100. Returning to FIG. 2B, the conductive pads 100 are isolated from one another (e.g., the conductive pad 100 associated with the first capacitive sensing component 42a is isolated from the conductive pad 100 associated with the second capacitive sensing component 42b), and are electrically connected to the corresponding second electrode plate 82 via a second conductor 102. As shown, each of the second conductors 102 projects through a thickness of the second housing structure 52, and in particular the base 72.

Assembly of the sensor 24 includes mounting of the first housing structure 50 to the second housing structure 52 as shown. Attachment of the housing structures 50, 52 can be accomplished in a variety of manners, for example, adhesive, welding, etc. Regardless, the inner and outer rims 62, 64 of the first housing structure 50 (or optionally the conductive material applied thereto) bear against the second housing structure 52 (e.g., the encapsulating layer 74 where provided). The electrode plates 80, 82 of each of the capacitive sensing components 42 are maintained in the spaced-apart fashion described above. The inner and outer rims 62, 64 of the first housing structure 50 effectively serve as beams, allowing the platform 60 of the first housing structure 50 to elastically flex inwardly toward the base 70 of the second housing structure 52. More particularly, in response to a force imparted upon the first housing structure 50, the central region(s) 66 move toward the base 70 via flexing of the platform 60, thereby decreasing a spacing of the gap 84. Thus, due to the inherent resilient flexibility of the housing 40, a variable gap is established for each of the capacitive sensing components 42, leading to a capacitance shift whenever a size of the gap 84 changes. As described below, this capacitance shift alters the resonating frequency of a corresponding LC circuit, with this alteration being indicative of the force applied to the housing 40.

Figure 4:
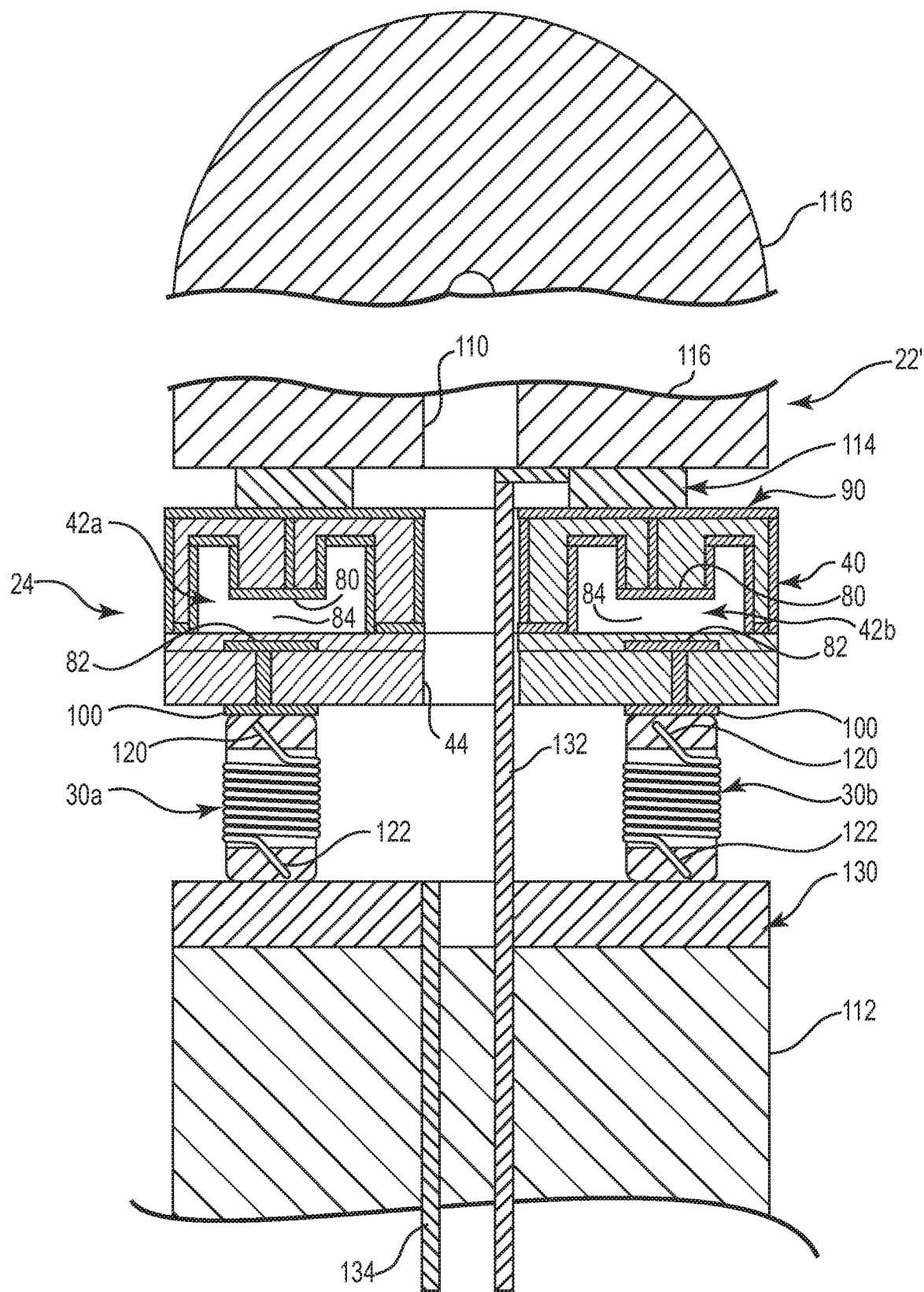
FIG. 4 is a simplified, cross-sectional view of the sensor of FIG. 2B assembled to an object.

The sensor 24 can be assembled to the object 22 (FIG. 1) in a variety of manners as a function of the characteristics of the object 22 in question. For example, FIG. 4 illustrates but one acceptable arrangement of the sensor 24 relative to an object 22', with the object 22' being an elongated tubular body. The tubular object 22' can have a variety of end-use applications, and in some constructions is a surgical instrument. For example, the object 22' can be a cannula, catheter, etc. Regardless, the object 22' defines a central lumen 110 and an outer diameter 112. The sensor 24 is sized in accordance with dimensions of the tubular body 22', having an outer diameter approximating the outer diameter 112 of the tubular body 22'. Further, the sensor 24 is arranged such that the central bore 44 is axially aligned with the central lumen 110. The housing 40 can be directly mounted to the tubular body 22'. Alternatively, a support 114, such as a metal support, can be attached to the common electrode 90 and in turn mounted (e.g., bonded) to the tubular body 22' as shown. The sensor 24 is located in close proximity to a segment of the tubular body 22' at which force measurements are desired. Thus, for example, where the tubular body 22' is a catheter terminating at a distal end 116 and forces at the distal end 116 are of interest, the sensor 24 is assembled in close proximity to the distal end 116. Alternatively, other locations relative to a length of the tubular body 22' (or other object 22 (FIG. 1)) are equally acceptable.

With additional reference to FIG. 1, the system 20 employs the inductors 30 to create an LC circuit with the capacitive sensing components 42. With the embodiment of FIG. 4, the inductors 30 are also assembled directly to the object 22' immediately adjacent the sensor 24. In this regard, individual ones of the inductors 30 are provided for respective ones of the capacitive sensing components 42 (e.g., where the sensor 24 includes three of the capacitive sensing components 42, three of the inductors 30 are provided). For example, in the view of FIG. 4, a first inductor 30a is associated with the first capacitive sensing component 42a, and a second inductor 30b is associated with the second capacitive sensing component 42b. With the but one acceptable construction of the sensor 24 that otherwise includes the conductive pads 100, a leading terminal 120 of each of the inductors 30 is electrically coupled to a corresponding one of the conductive pads 100. Thus, for example, the leading terminal 120 of the first inductor 30a is electrically connected (e.g., mounted to) the conductive pad 100 associated with the first capacitive sensing component 42a. To minimize the number of wires required with the system 20, an optional second common electrode 130 (e.g., metal support ring) is electrically coupled to a trailing terminal 122 of each of the inductors 30, and is assembled to the object 22'. With this construction, then, a first wire 132 is electrically connected to, and extends from, the first common electrode 90, and a second wire 134 is electrically connected to, and extends from, the second common electrode 130.

The wires 132, 134 can be embedded within, and/or extend within the lumen 110 of, the tubular object 22'. Alternatively, one or both of the wires 132, 134 can extend along an exterior of the tubular object 22'. Similarly, where the object 22' in question is something other than a tubular body, one or both of the wires 132, 134 can be embedded within a thickness of the object and/or extend along an exterior thereof. Regardless, and with additional reference to FIG. 1, the first wire 132 electrically connects the sensor 24, and in particular the capacitive sensing components 42, with the energy source 26; the second wire 134 electrically connects the sensor 24, via the inductors 30, with the detector 28. The LC circuit thus established by the above connections is shown in FIG. 5.

Figure 5:
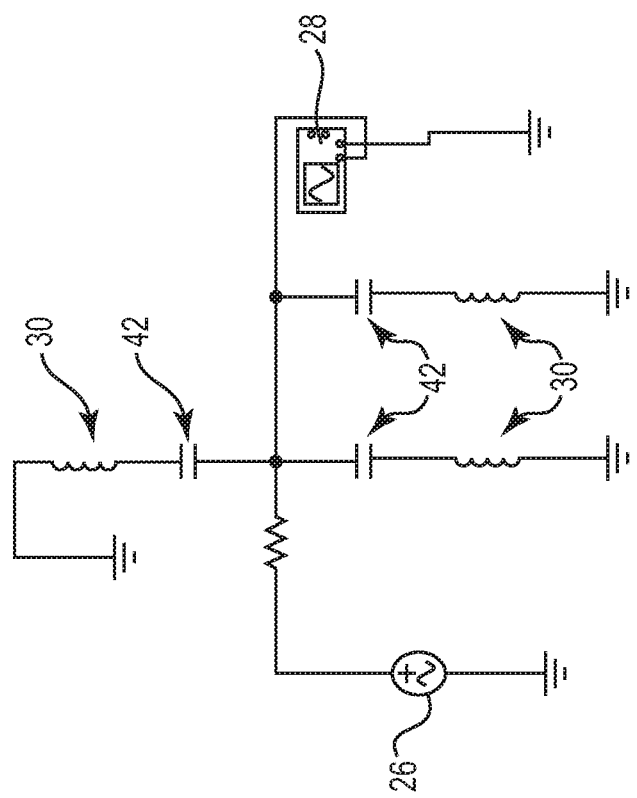
FIG. 5 is a circuit diagram of the system of FIG. 1.

With continued reference to FIGS. 4 and 5, the system 20 can operate based on the principle of applied pressure on the distal end 116 of the object 22' being transferred onto the sensor housing 40 that in turn changes a size of the gap 84 between the electrode plates 80, 82 of one or more of the sensing component 42 and leads to a capacitance shift. This shift, in turn, alters the resonating frequency of the LC circuit. For example, the energy source 26 (e.g., a frequency generator) can be configured to apply a sweeping voltage to the sensor 24/capacitive sensing components 42. The resultant impedance of the LC circuit as affected by the capacitive sensing components 42 is delivered as an output signal via the second wire 134 to the detector 28. In some constructions, the detector 28 can be an impedance measuring device. The impedance detector 28 (or a computer (not shown) connected to the detector 28) can plot impedance in the frequency domain, and the change of the frequency pitches in response to an applied force upon the distal end 116 of the object 22' reflects the magnitude and direction of the applied force. Thus, the principle of measurement of the impedance is to measure the current by an applied sweeping voltage.

Figure 6A:
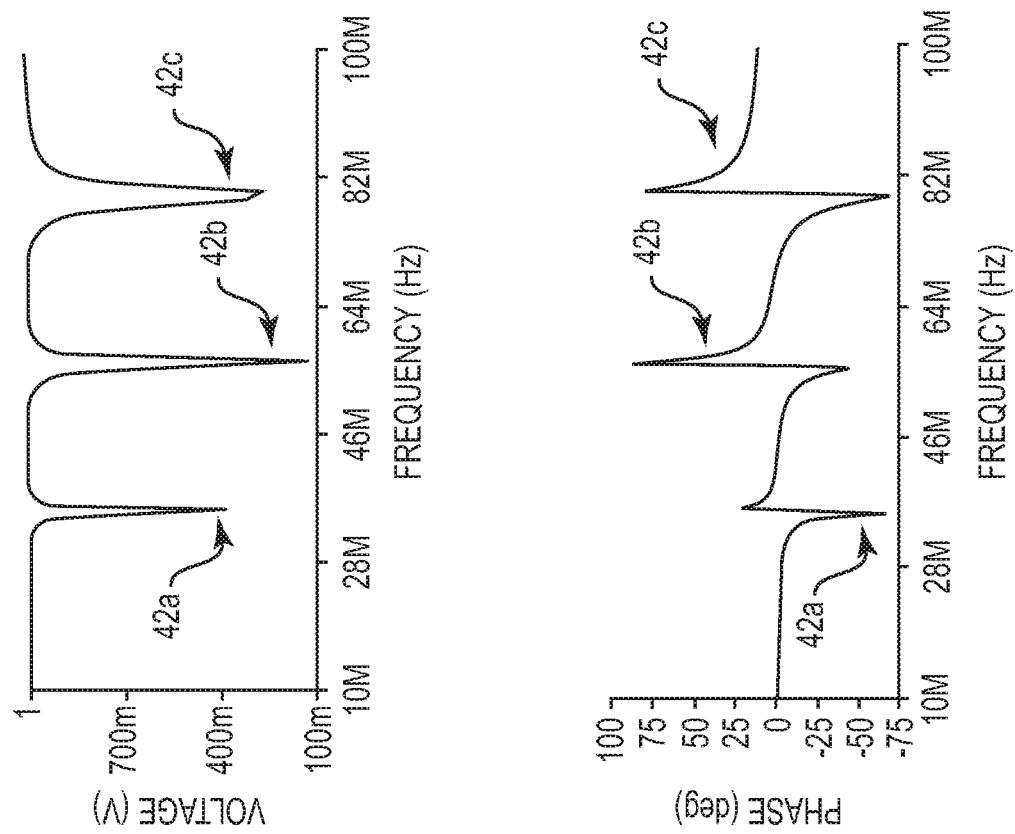
FIG. 6A are graphs of a baseline output signal generated by one example force detection system in accordance with principles of the present disclosure in a normal or at rest state.

For example, FIG. 6A is a representative plot of voltage and of phase in the frequency domain for an example force detection system 20 of FIG. 1 in accordance with the present disclosure incorporating three of the capacitive sensing components 42 (FIG. 2B) each having a capacitance of 4 pF in a normal or "at rest" state of the sensor 24 (i.e., no external force being applied to the object to which the sensor 24 is assembled such that the housing 40 is not deflected). With this example, the sensor 24 is a cylindrical ring, having an outer diameter on the order of 2.3 mm, an inner diameter on the order of 1.1 mm, and a height on the order of 0.5 mm (it being understood the present disclosure is in no way limited to these dimensions; sensors in accordance with the present disclosure can be larger or smaller, and need but be a ring). The energy source 26 (FIG. 1) applies energy at 1 V/100 MHz/0 deg. "Spikes" in the voltage and phase plots shown in FIG. 6A represent the affect of the three capacitive sensing components 42 (labeled as 42a, 42b, 42c in FIG. 6A) upon the output signal as delivered to the detector 28. The spike magnitude and frequency of FIG. 6A reflect baseline values for the capacitive sensing components 42a-42c.

Figure 6B:
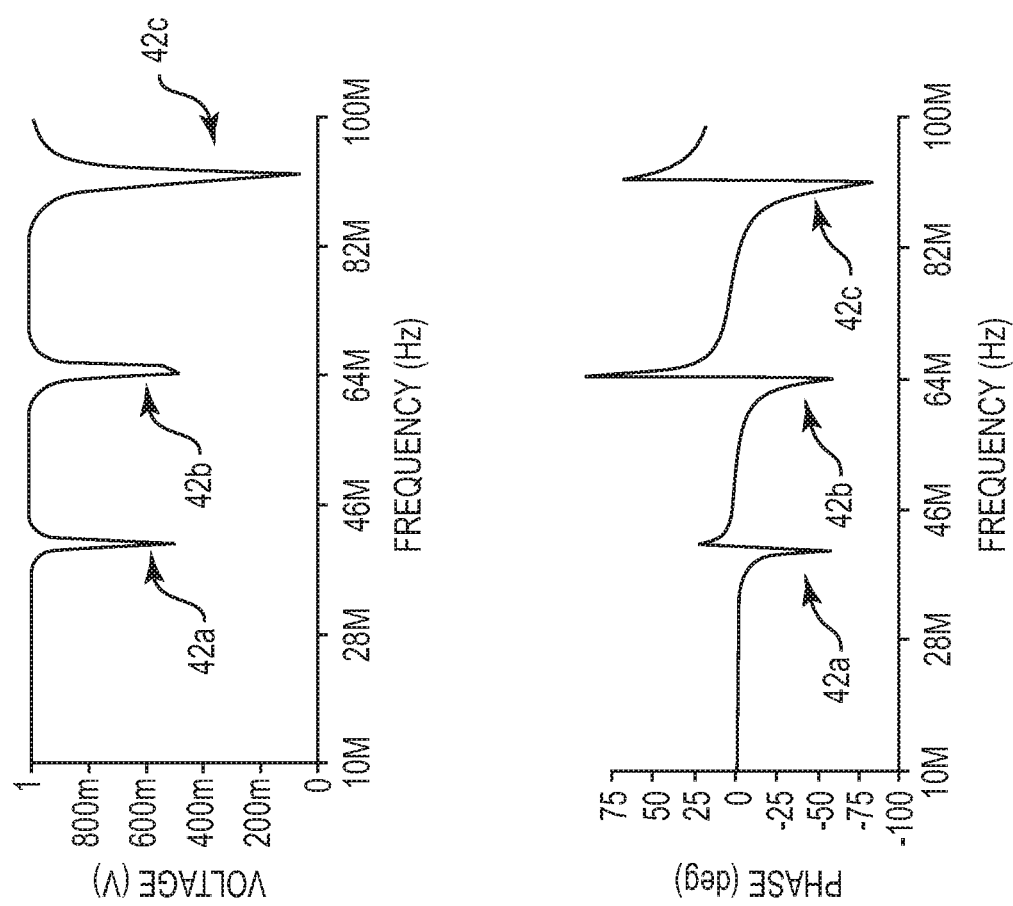
FIGS. 6B and 6C are graphs illustrating output signals during use of the system of the present disclosure in estimating magnitude and direction of force in comparison with the output signal of FIG. 6A.

FIG. 6B provides a plot of the voltage and phase values in the frequency domain in the same example system wherein the object to which the sensor 24 is assembled is subjected to a simulated external force or pressure. The simulated force will cause the housing 40 (FIG. 2B) to deflect, thereby changing a gap spacing (and thus capacitance of one or more of the sensing components 42a-42c,) with the affects of the capacitive sensing components 42a-42c identified in the graphs. The "spikes" in the output signal of FIG. 6B differ from the normal or baseline state/signal of FIG. 6A due to the reduction in size of the gaps 84 associated with the capacitive sensing components 42a-42c. By comparing differences between the "spikes" in the currently-received output signal (i.e., FIG. 6B) with the baseline values (i.e., FIG. 6A), a determination can be made as to a magnitude of the force being applied onto the object 22'. Similarly, because the capacitive sensing components 42a-42c are, in some embodiments, arranged in a known configuration relative to one another (circular, triangular, etc.), the comparison of "spikes" in the currently-received output signal are indicative of a direction of the force (e.g., via triangulation). As a point of reference, upon removal of the external force, the housing 40 will naturally revert back to the "normal" or at rest state; the capacitive sensing elements 42a-42c and corresponding output signal thus also return to the baseline state.

Figure 6C:
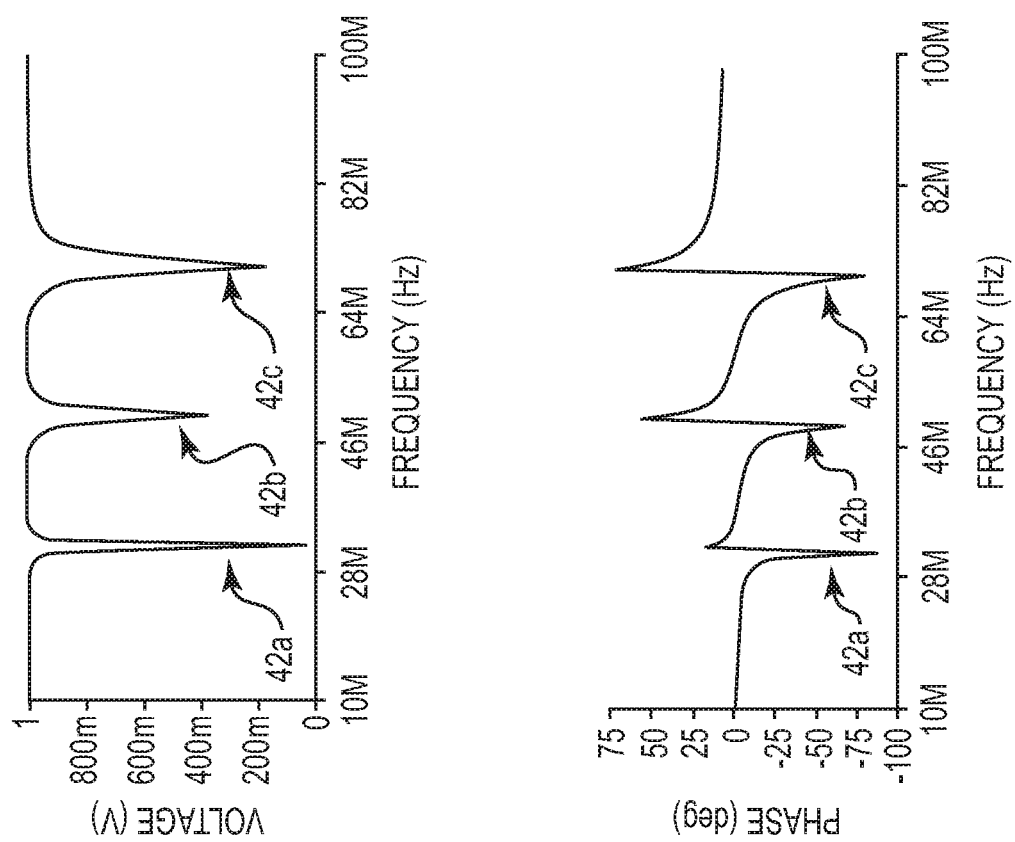

FIG. 6C illustrates another plot of an output signal generated by the example system described above in response to a simulated force applied to the object to which the sensor 24 is assembled. The affect on the output signal by the capacitive sensing elements 42a-42c is labeled in FIG. 6C; once again, by comparing the currently-received output signal (and in particular, the "spikes" associated with the capacitive sensing elements 42a-42c) with the baseline values of the normal state (of FIG. 6A), a determination of magnitude and direction of the force applied to the object can be made.

Figure 7:
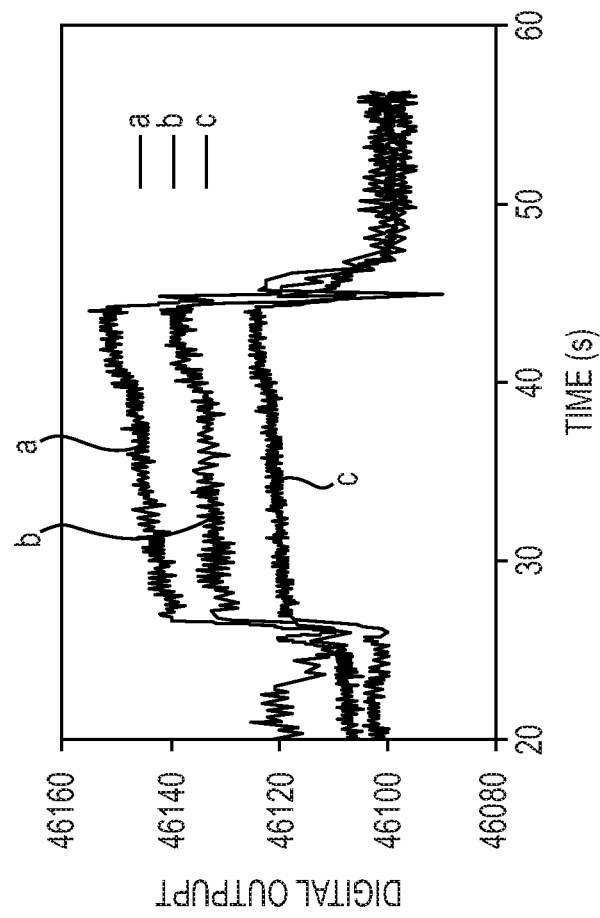
FIG. 7 schematically illustrates estimation of force direction in accordance with principles of the present disclosure.
Figure 7:
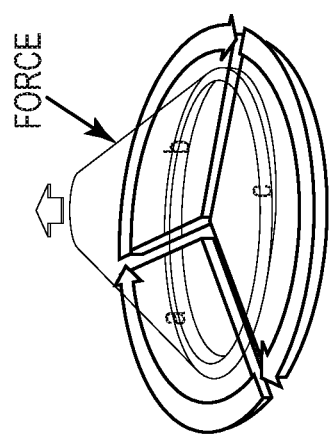

The evaluation of magnitude and direction of applied force as described above is but one acceptable technique in accordance with the present disclosure. The output signal(s) generated by the sensor 24 can be analog or digital. For example, a schematical representation of a force direction determination based on a digital output signal is provided in FIG. 7. A user can manually review the signal(s) and make force determinations. Alternatively, a computing device can automatically estimate or calculate force magnitude and direction. Further, the system 20 can be calibrated prior to use; for example, the sensor 24 can be subjected to various, known forces and the subsequent affect on the output signal noted and utilized to calibrate the force evaluation during actual use.

Figure 8A:
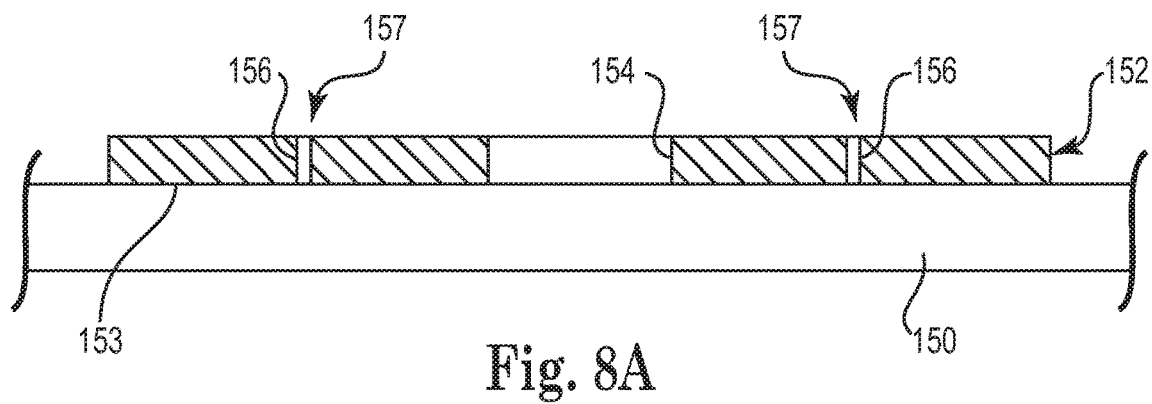
FIGS. 8A-8F are schematic illustrations of a process flow for constructing a portion of the sensor of FIG. 2B.

Returning to FIG. 2A, the sensor 24 can be manufactured in a variety of manners, and in some embodiments is constructed based on microelectromechanical systems (MEMS)-based technology. For example, FIGS. 8A-8F schematically illustrate one embodiment of an MEMS process flow for constructing the first housing structure 50 (FIG. 2B). In FIG. 8A, a substrate 150 (e.g., a silicon wafer) is provided, and a base layer 152 of the desired non-conductive material (e.g., polymer as described above) is formed thereon. A bottom face 153 of the base layer 152 is in contact with the substrate 150. With embodiments in which the resultant sensor 24 (FIG. 2A) is a cylindrical ring, the base layer 152 is formed along the substrate 150 to have a ring-like shape, defining a central aperture 154. Further, a plurality of longitudinal passages 156 are defined through a thickness of the base layer 152 at locations where the capacitive sensing components will reside (e.g., where the resultant sensor 24 will be constructed to provide three, equidistantly spaced sensing components, three of the passages 156 are formed in the base layer 152 equidistantly spaced from one another relative to a circumference of the base layer 152). Thus, the base layer 152 can be described as having theoretical capacitive sub-assembly sections 157 at which the passages 156 are formed.

Figure 8B:
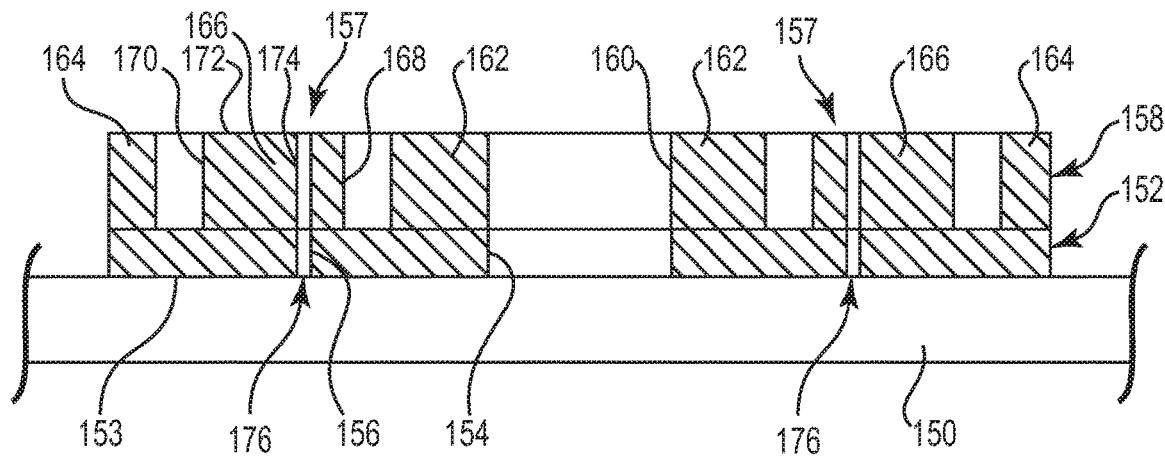

An intermediate layer 158 of the non-conductive material is then formed on the base layer 152 as shown in FIG. 8B. Commensurate with the base layer 152, the intermediate layer 158 is also ring-shaped, and defines a central aperture 160 that is otherwise axially aligned with the central aperture 154 of the base layer 152. In this regard, the intermediate layer 158 is formed to define an inner ring segment 162, an outer ring segment 164, and a plurality of circumferentially spaced central segments 166. The central segments 166 correspond with the capacitive sub-assembly sections 157 as described above. Relative to the cross-sectional view of FIG. 8B, then, each of the central segments 166 is defined by opposing, first and second circumferential sides 168, 170. The first circumferential side 168 faces, but is radially spaced from, the inner ring segment 162; similarly, the second circumferential side 170 faces, but is radially spaced from, the outer ring segment 164. Further, each of the central segments 166 forms a top face 172 opposite the base layer 152, and a passage 174 extending through a thickness thereof. The passage 174 corresponds and is aligned with the corresponding passage 156 in the base layer 152 such that a through hole 176 is provided within each capacitor sub-assembly section 157 extending between, and open relative to, the bottom face 153 of the base layer 152 and the top face 172 of the central segment 166.

Figure 8C:
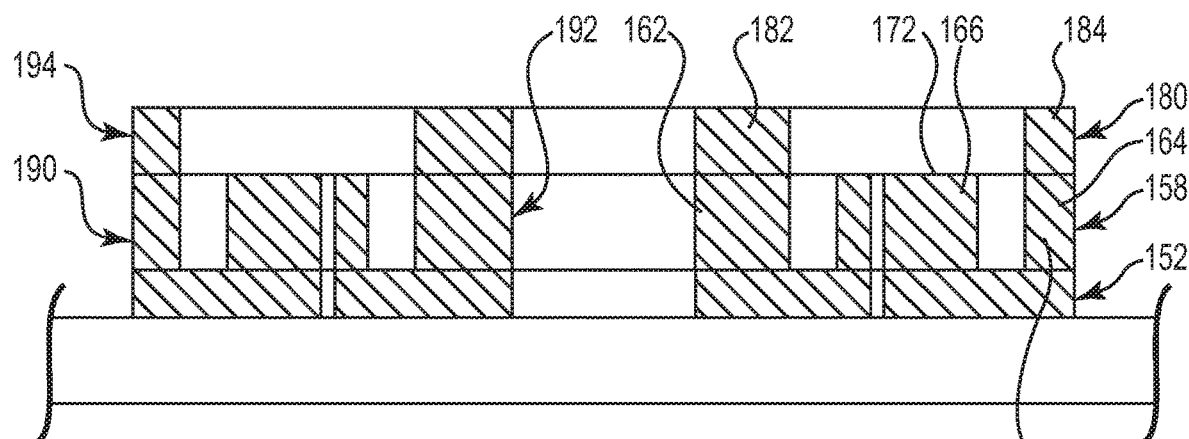

A third layer 180 of the non-conductive material is formed on the intermediate layer 158 as shown in FIG. 8C. The third layer 180 is formed to generally correspond with the inner and outer ring segments 162, 164 of the intermediate layer 158, and thus includes an inner ring 182 and an outer ring 184. As shown, the third layer 180 is not formed over the top face 172 of the central segments 166. Regardless, a support structure 190 is collectively formed by the layers 152, 158, 180, and has inner circumferential surface 192 and an outer circumferential surface 194.

Figure 8D:
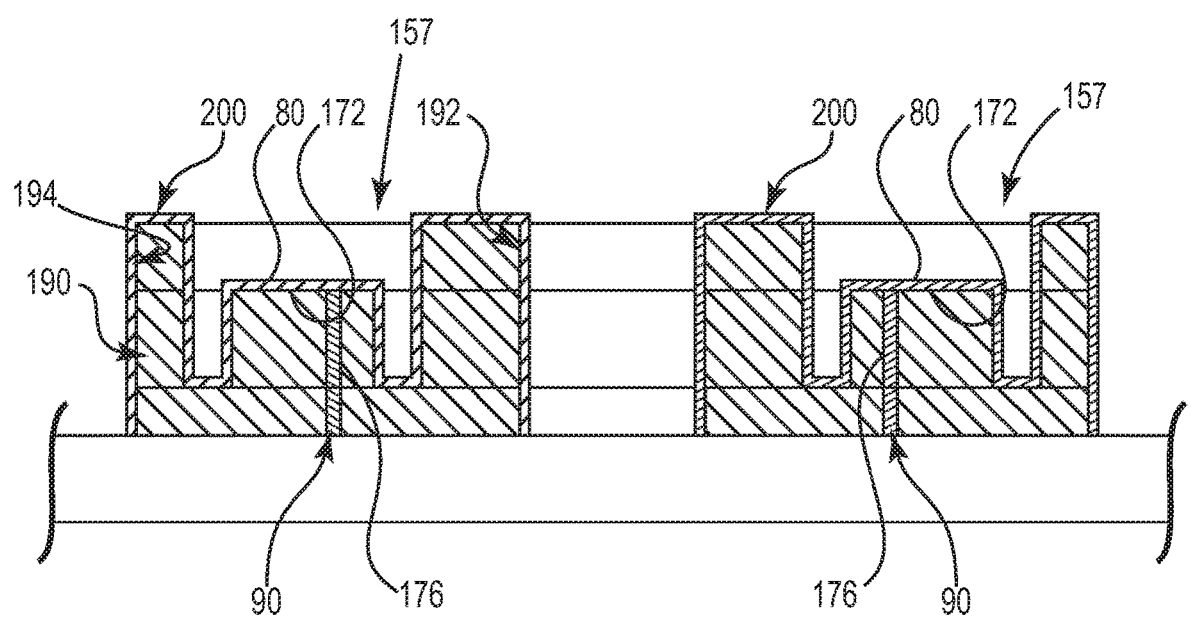

An electrically-conductive material 200, such as a metal (e.g., chromium/gold) as described above, is then deposited (e.g., sputtered) onto exposed surfaces of the support structure 190 as shown in FIG. 8D. The conductive material 200 is applied to the top face 172 of each of the capacitive sub-assembly sections 157, thereby forming the first electrode plate 80 as described above. The conductive material 200 can also be deposited onto other surfaces of the support structure 190, for example one or both of the inner and outer circumferential surfaces 192, 194. Further, the conductive material 200 is deposited within each of the through holes 176 to form the conductors 90 as described above. In some embodiments, the conductive material 200 can include an inner layer of a sputter coated first material (e.g., 20 nm thick chromium) and an outer layer of a sputter coated material (e.g., 200 nm thick gold).

Figure 8E:
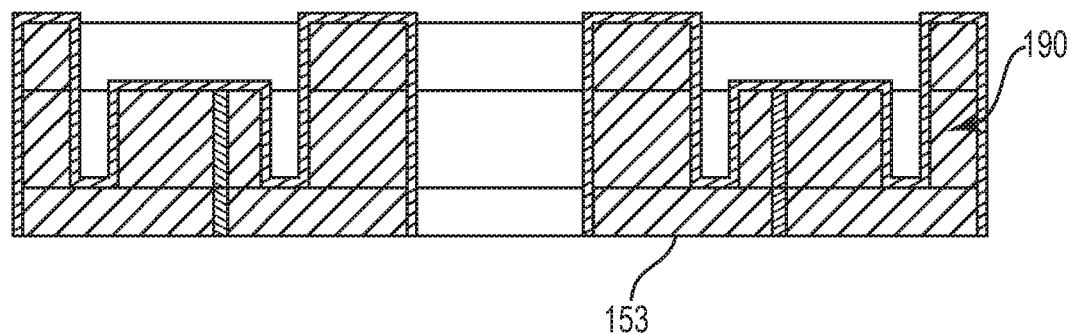
Figure 8F:
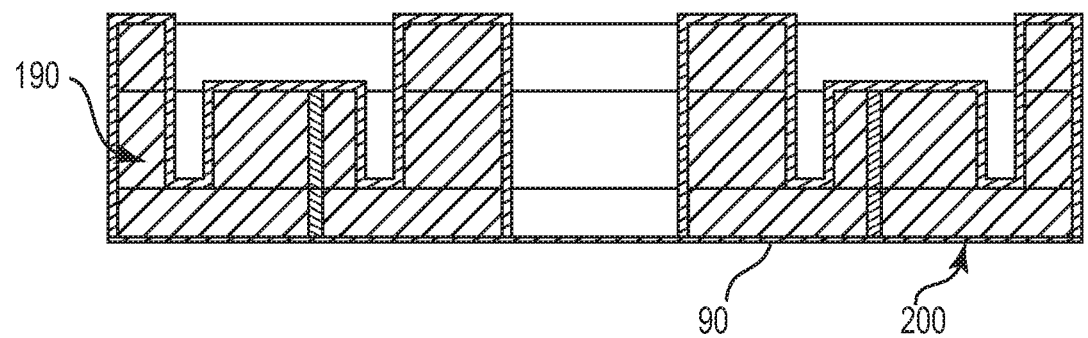

The support structure 190 is then removed from the substrate 150 as shown in FIG. 8E. The electrically-conductive material 200 is then deposited (e.g., sputtered) onto the now-exposed bottom face 153 of the support structure 190 as shown in FIG. 8F thereby forming the common electrode 90 described above.

Figure 9A:
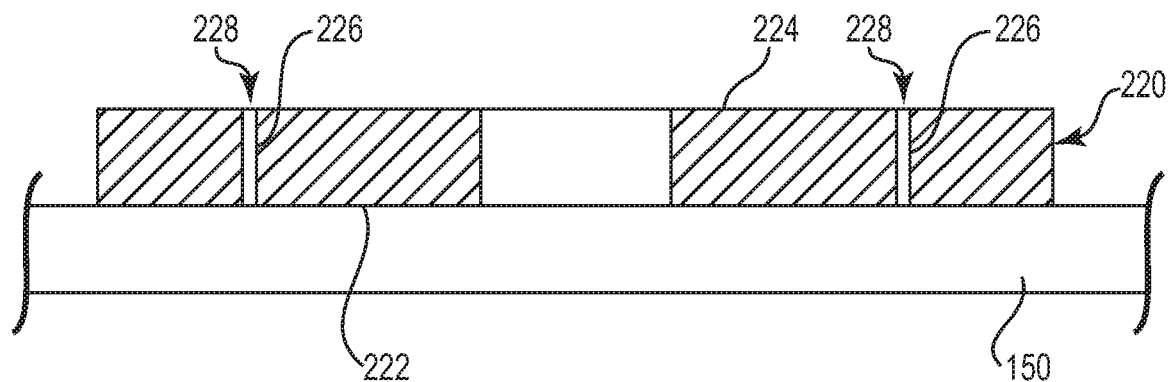
FIGS. 9A-9F schematically illustrate a process flow for constructing another portion of the sensor of FIG. 2B.

A similar MEMS processing technique can be employed to form the second housing structure 52 (FIG. 2B) as shown in FIGS. 9A-9F. In general terms, a first layer 220 of the selected non-conductive material is formed on the substrate 150 and includes a bottom face 222 and a top face 224 as shown in FIG. 9A. A plurality of through holes 226 are defined through a thickness of the first or base layer 220, corresponding with desired location and spacing of the later-formed capacitor electrode plates. Thus, the first layer 220 can be described as having theoretical capacitive sub-assembly sections 228 at which respective ones of the through holes 226 are defined.

Figure 9B:
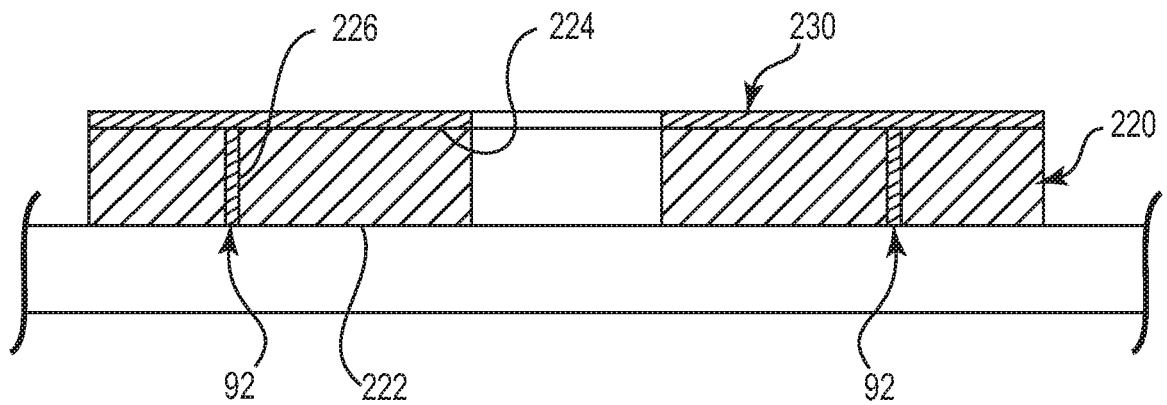

In FIG. 9B, an electrically-conductive material 230, such as a metal (e.g., chromium/gold) as previously described, is deposited (e.g., sputtered) to the top face 224. In addition, the conductive material 230 is deposited within the through holes 226, extending between the bottom face 222 and the top face 224, to form the conductors 92 (FIG. 2B).

Figure 9C:
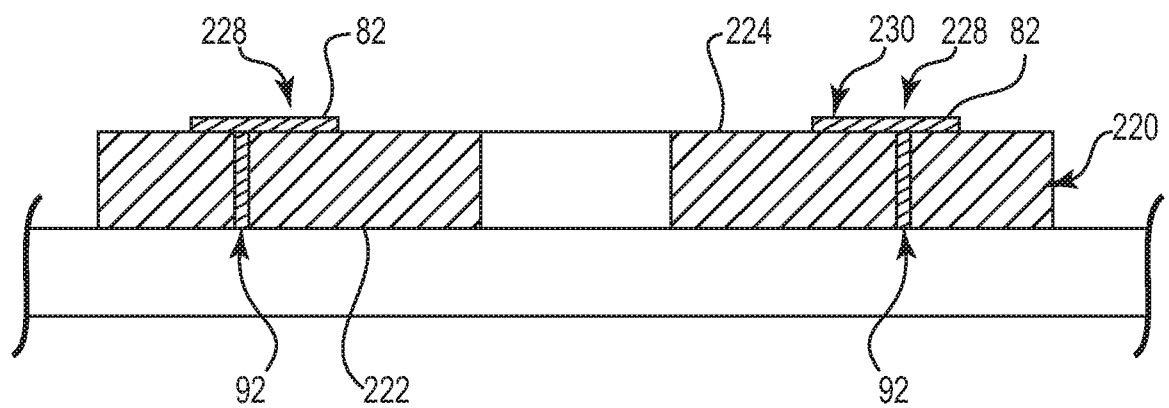

As shown in FIG. 9C, a portion of the deposited conductive material 230 is removed from areas of the top face 224 apart from the capacitive sub-assembly sections 228, resulting in the circumferentially spaced electrode plates 82. Alternatively, the conductive material 230 can be initially deposited only at the desired electrode plate 82 regions of the top face 224. Regardless, the circumferentially spaced electrode plates 82 are defined and are electrically connected to the bottom face 222 via the conductors 92.

Figure 9D:
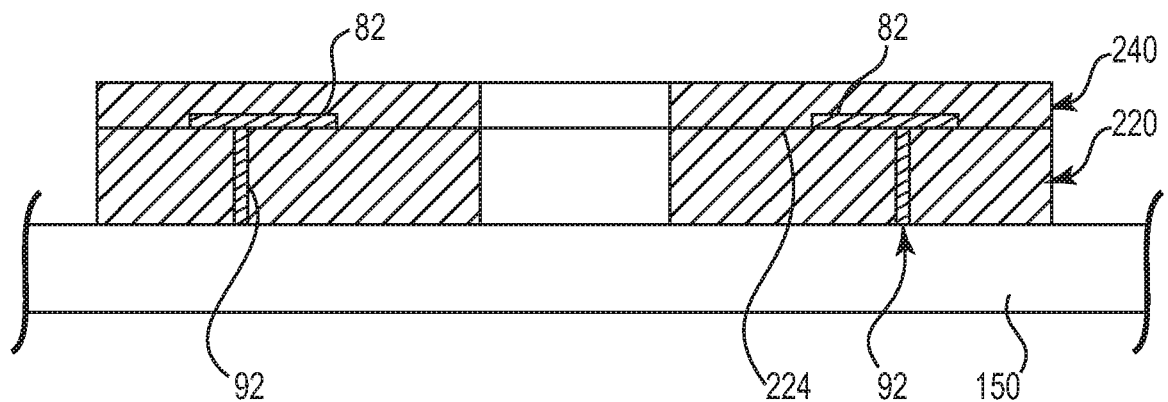

In some constructions and with reference to FIG. 9D, a second layer 240 of the non-conductive material is subsequently formed onto the top face 224 of the base layer 220, and encompasses the electrode plates 82. As described above, the second layer 240 encapsulates the electrode plates 82 and corresponding conductors 92 (FIG. 2B) from possible electrical shorts in the presence of a high shock force. Alternatively, the second layer 240 can be omitted.

Figure 9E:
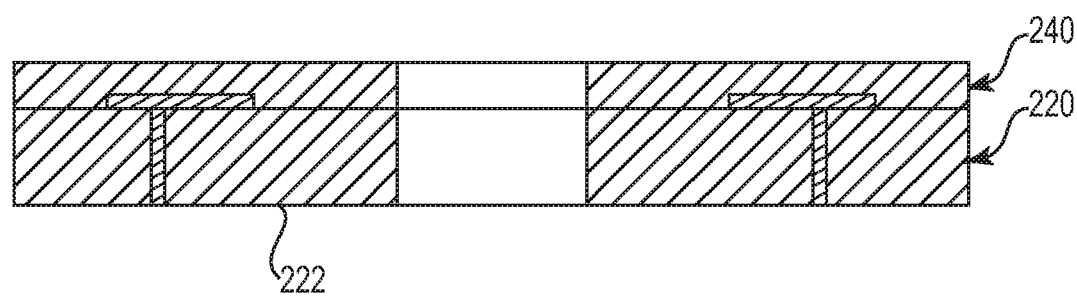
Figure 9F:
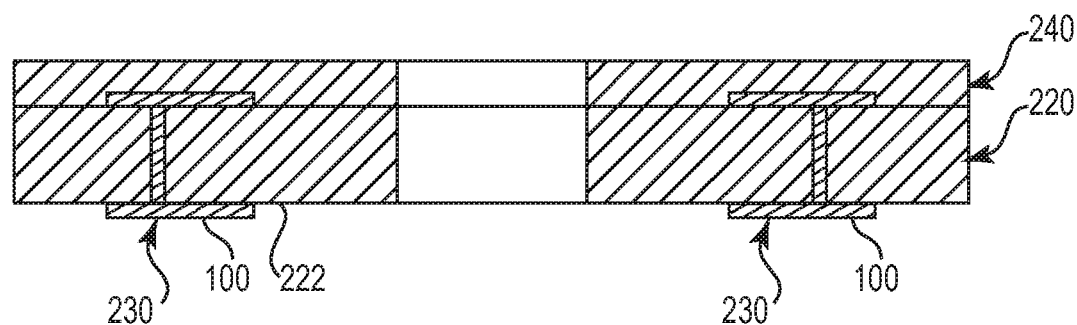

Regardless, and as shown in FIG. 9E, the first layer 220 is removed from the substrate 150. In FIG. 9F, the electrically-conductive material 230 is deposited (e.g., sputtered) onto the now-exposed bottom face 222 and formed to define the circumferentially spaced conductive pads 100 (FIG. 2B) as described above.

The housing structures 50, 52 (FIG. 2B) can be formed in a variety of manners differing from those described above. For example, other MEMS process flows are available. Alternatively, where the sensor 24 is of a larger size, conventional molding/fabrication is also envisioned. In some embodiments, upon final construction, the housing parts 50, 52 are assembled to one another (e.g., epoxy or glue) as previously described, resulting in the sensor 24.

Figure 10:
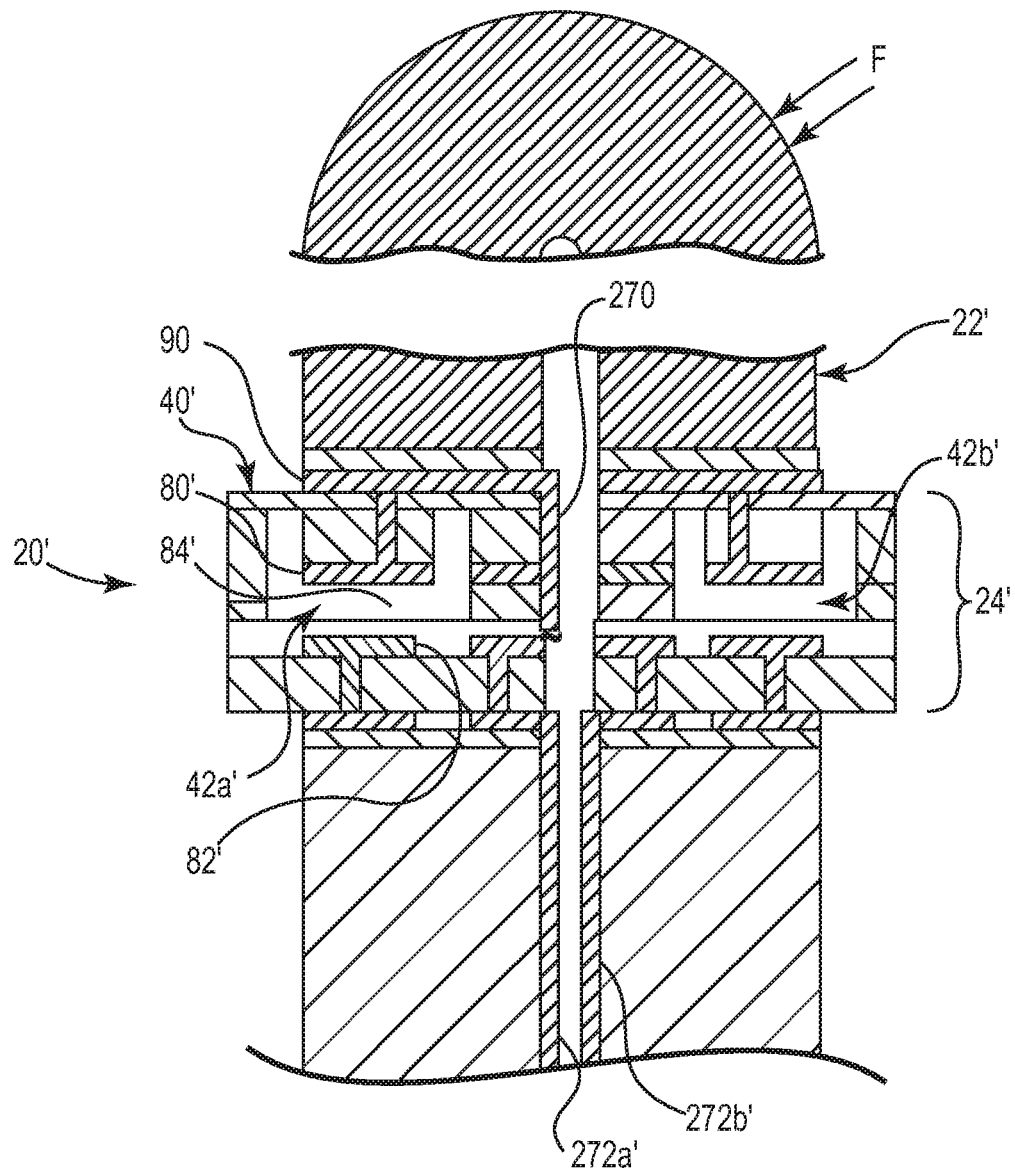
FIG. 10 is a simplified, cross-sectional view of a portion of an alternative force detection system in accordance with principles of the present disclosure and assembled to an object.

Returning to FIG. 1, while the system 20 has been described as incorporating the inductors 30 directly into the object 22, in other constructions, the inductors 30 can be located discrete of the object 22 (and thus of the sensor 24). With these constructions, three or more wires may be required as generally indicated by the alternative system 20' construction of FIG. 10. The system 20' includes a sensor 24' assembled to the object 22'. As with previous embodiments, the sensor 24' includes a housing 40' and three or more capacitive sensing components 42' (two of which are illustrated in FIG. 10). A first wire 270 electrically connects the common electrode 90 of the sensor 24' with the energy source 26 (FIG. 1). Further, a separate wire 272 is provided for each of the capacitive sensing components 42' (e.g., wire 272a is electrically connected to the first capacitive sensing component 42a' and wire 272b is electrically connected to the second capacitive sensing component 42b'). The capacitor wires 272 extend from the object 22' and are electrically connected to a respective one of the inductors (not shown) otherwise provided apart from the object 22. The inductors, are, in turn, electrically connected to the detector 28 (FIG. 1), with signals from the inductors combining to provide the output signal analyzed by the detector 28 as described above.

The system 20' operates in a manner highly akin to those described above, with the capacitance associated with one or more of the capacitive components 42' changing in response to a force applied to the object 22', and thus to the housing 40'. That is to say, a size of the gap 84' defined between electrode plates 80', 82' of one or more of the capacitive sensing components 42' changes in response to the force F; this change is size alters the impedance value associated with the corresponding LC circuit. This alteration is indicative of a magnitude of the applied force F, and the changes in each of the capacitive sensing component outputs collectively indicate a direction of the force F. Based upon these same principles, in other embodiments, the inductors can be omitted.

The force detection systems and methods of the present disclosure provide a marked improvement over previous designs. The sensors are highly amenable to small scale applications (e.g., on the order of 5 mm or less), and can be employed with surgical instrumentation (e.g., catheters). Further, testing has confirmed that even at small scale constructions (e.g., on the order of 5 mm or less), the sensors of the present disclosure generate reliable force-related results at temperatures exceeding 65° C. and can withstand and continue to generate reliable results (e.g., sensing forces in the range of 1-200 grams) after experiencing shock forces on the order of 200 grams. Further, the sensors can be fabricated on a mass-production (and thus low cost) basis utilizing MEMS technology, with multiple flexible, tri-axes force sensors being generated on a single silicon wafer.

Although the present disclosure has been described with reference to preferred embodiments, workers skilled in the art will recognize that changes can be made in form and detail without departing from the spirit and scope of the present disclosure.

What is claimed is:

1. A force sensing medical catheter, comprising:
   an elongated tubular body comprising a central lumen and a distal end; and
   a sensor comprising a first sensor part, a second sensor part, and a housing;
   wherein the first sensor part comprises a common electrode and wherein the second sensor part comprises at least three capacitive sensing components,
   wherein the first sensor part and the second sensor part are configured to be assembled such that the common electrode and each of the at least three capacitive sensing components establish a variable gap therebetween, wherein the housing surrounds the variable gap, and
   wherein the variable gap is configured to vary in response to a force acting upon the distal end.

2. The force sensing medical catheter of claim 1, further comprises at least three inductors, wherein each of the at least three capacitive sensing components is electrically coupled to one of the at least three inductors.

3. The force sensing medical catheter of claim 2, wherein the at least three inductors are coupled to the sensor.

4. The force sensing medical catheter of claim 1, further comprising at least three electrical wires, and wherein each of the at least three electrical wires is connected to one of the at least three capacitive sensing components.

5. The force sensing medical catheter of claim 1, wherein an output signal from the sensor varies as a function of the force acting upon the distal end.

6. The force sensing medical catheter of claim 1, wherein the sensor further comprises a cylindrical ring defining a central bore.

7. The force sensing medical catheter of claim 6, wherein the central bore is arranged to align with the central lumen.

8. The force sensing medical catheter of claim 1, wherein the sensor is configured to have a degree of elastic flexibility.

9. The force sensing medical catheter of claim 1, wherein the common electrode and the at least three capacitive sensing components each comprises a sputter-coated material.

10. The force sensing medical catheter of claim 1, wherein each of the at least three capacitive sensing components comprises an arcuate shape.

11. The force sensing medical catheter of claim 10, wherein the at least three capacitive sensing components are arranged in a circular pattern.

12. The force sensing medical catheter of claim 1, wherein the common electrode comprises a ring shape.

13. A force sensor for a medical device, comprising:
a first sensor part, a second sensor part, and a housing,
wherein the first sensor part and the second sensor part comprise a biologically inert material,
wherein the first sensor part comprises a common electrode and wherein the second sensor part comprises at least three capacitive sensing components,
wherein the first sensor part and the second sensor part are configured to be assembled such that the common electrode and each of the at least three capacitive sensing components establish a variable gap therebetween, wherein the housing surrounds the variable gap, and
wherein the variable gap is configured to vary in response to a force acting upon a distal end of the force sensor.

14. The force sensor for a medical device of claim 13, further comprising at least three inductors, wherein each of the at least three capacitive sensing components is coupled to one of the at least three inductors.

15. The force sensor for a medical device of claim 13, wherein the first sensor part and the second sensor part each comprise a cylindrical ring defining a central bore.

16. The force sensor for a medical device of claim 13, wherein the sensor is configured to have a degree of elastic flexibility.

17. The force sensor for a medical device of claim 13, wherein an output signal from the force sensor varies as a function of the force acting upon the distal end.

18. The force sensor for a medical device of claim 13, wherein the common electrode and the at least three capacitive sensing components each comprises a sputter-coated material.

19. The force sensor for a medical device of claim 13, wherein each of the at least three capacitive sensing components comprises an arcuate shape.

20. The force sensor for a medical device of claim 13, wherein the common electrode comprises a ring shape.

* * * * *